US010456536B2

(12) United States Patent
Van De Laar et al.

(10) Patent No.: US 10,456,536 B2
(45) Date of Patent: Oct. 29, 2019

(54) INHALER WITH TWO MICROPHONES FOR DETECTION OF INHALATION FLOW

(71) Applicant: KONINKLIJKE PHILIPS N.V., Eindhoven (NL)

(72) Inventors: Jakob Van De Laar, Oosterhout (NL); Rene Martinus Maria Derkx, Eindhoven (NL); Cornelis Pieter Janse, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 489 days.

(21) Appl. No.: 15/128,605

(22) PCT Filed: Mar. 12, 2015

(86) PCT No.: PCT/EP2015/055117
§ 371 (c)(1),
(2) Date: Sep. 23, 2016

(87) PCT Pub. No.: WO2015/144442
PCT Pub. Date: Oct. 1, 2015

(65) Prior Publication Data
US 2017/0100550 A1      Apr. 13, 2017

(30) Foreign Application Priority Data
Mar. 25, 2014   (EP) .................................... 14161419

(51) Int. Cl.
*A61M 15/00*    (2006.01)
*A61B 5/087*    (2006.01)
(Continued)

(52) U.S. Cl.
CPC ......... *A61M 15/0021* (2014.02); *A61B 5/087* (2013.01); *A61B 5/7203* (2013.01);
(Continued)

(58) Field of Classification Search
CPC .............. A61M 15/00; A61M 15/0021; A61M 15/0065; A61M 15/008; A61M 15/009;
(Continued)

(56) References Cited

U.S. PATENT DOCUMENTS 5,331,953 A *  7/1994  Andersson ............ A61M 15/00
                                                           128/200.14
6,526,976 B1   3/2003  Baran
(Continued)

FOREIGN PATENT DOCUMENTS

EP      0617628 B1    5/1998
EP      1290912 A2    3/2003
(Continued)

OTHER PUBLICATIONS

Widrow B. et al., "Adaptive Switching Circuits," IRE WESCON Conv.Rec., 1960, vol. part 4, pp. 96-104.
(Continued)

*Primary Examiner* — Kathryn E Ditmer
(74) *Attorney, Agent, or Firm* — Michael W. Haas

(57) ABSTRACT

An inhaler with a housing (H) comprising an air-inlet (A_I) and a an air-outlet (A_O). Inside the housing (H) a flow path (FP) is defined between air-inlet (A_I) and air-outlet (A_O) where a dispenser (DP) is arranged to dispense an aerosol or a dry powder in the flow path (FP). Two sensors (S1, S2), e.g. microphones, are positioned spaced apart at external surfaces of the housing (H) to sense sound or vibrations resulting from a flow in the flow path (FP) at two different positions. This allows a precise detection of flow velocity during inhalation based on the sound or vibrations sensed by the two sensors (S1, S2), thus allowing examination of correct use of the inhaler. Further, the use of two spaced apart sensors (S1, S2) facilitates identification of priming and firing events in the sensed sound or vibrations which
(Continued)

may also be used in evaluating the use of the inhaler. Preferably, a noise reduction algorithm is used that exploits the differences in the captured sound or vibrations from the two sensors (S1, S2), so at to allow precise flow measurements even in noisy environments.

15 Claims, 10 Drawing Sheets

(51) Int. Cl.
*A61B 5/00* (2006.01)
*G09B 19/00* (2006.01)
*G09B 23/28* (2006.01)
*A61M 16/00* (2006.01)

(52) U.S. Cl.
CPC .......... *A61M 15/00* (2013.01); *A61M 15/009* (2013.01); *G09B 19/00* (2013.01); *G09B 23/28* (2013.01); *A61B 2560/0242* (2013.01); *A61M 2016/0021* (2013.01); *A61M 2202/064* (2013.01); *A61M 2205/332* (2013.01); *A61M 2205/3306* (2013.01); *A61M 2205/3317* (2013.01); *A61M 2205/3331* (2013.01); *A61M 2205/3334* (2013.01); *A61M 2205/3375* (2013.01); *A61M 2205/3569* (2013.01); *A61M 2205/3592* (2013.01); *A61M 2205/50* (2013.01); *A61M 2205/505* (2013.01); *A61M 2205/52* (2013.01); *A61M 2205/58* (2013.01)

(58) Field of Classification Search
CPC ..... A61B 5/087; A61B 5/7203; A61B 5/7214; G01P 5/24–5/245
See application file for complete search history.

(56) References Cited

U.S. PATENT DOCUMENTS

| | | | |
|---|---|---|---|
| 2004/0069301 A1 | 4/2004 | Bacon | |
| 2009/0308387 A1* | 12/2009 | Andersen | A61M 15/00 128/203.15 |
| 2009/0314292 A1* | 12/2009 | Overfield | A61B 5/087 128/203.15 |
| 2011/0226237 A1 | 9/2011 | Morrison | |
| 2011/0253138 A1 | 10/2011 | Briant | |
| 2013/0151162 A1* | 6/2013 | Harris | A61M 15/00 702/19 |
| 2013/0172690 A1* | 7/2013 | Arne | A61M 15/009 600/301 |
| 2013/0317379 A1* | 11/2013 | Brimer | A61B 5/087 600/538 |
| 2014/0158126 A1* | 6/2014 | Parry-Billings | A61M 15/0093 128/203.15 |
| 2015/0231343 A1* | 8/2015 | Reilly | A61M 15/0033 128/202.22 |
| 2016/0166766 A1* | 6/2016 | Schuster | G06F 19/3468 702/54 |

FOREIGN PATENT DOCUMENTS

| | | |
|---|---|---|
| EP | 19993642 A1 | 11/2008 |
| GB | 2398065 A | 11/2004 |
| JP | 2013516265 A | 5/2013 |
| RU | 2141351 C | 11/1999 |
| WO | WO9526212 A1 | 10/1995 |
| WO | WO9850095 A1 | 11/1998 |
| WO | WO0191513 A2 | 11/2001 |
| WO | WO2007101438 A1 | 9/2007 |
| WO | WO2011083377 A1 | 7/2011 |
| WO | WO2012123448 A1 | 9/2012 |
| WO | WO2014033229 A1 | 3/2014 |

OTHER PUBLICATIONS

Boll, S.F. et al., "Suppression of Acoustic Noise in Speech using Spectral Subtraction," IEEE Transactions on Acoustics Speech and Signal Processing, vol. 27, pp. 113-120, Apr. 1979.

Harver A. et al., "Asthma, Health and Society, A Public Health Perspective", Springer, 2010, Chapter 6: Medical Management of Asthma by Andrej Petrov and Sally. E. Wenzel.

Dolovich, M.B. et al., "Aerosol Drug Delivery: Developments in Device Design and Clinical Use," The Lancet, vol. 377, pp. 1032-1045, Mar. 2011.

Moussavi Z. et al., "Fundamentals of Respiratory Sounds and Analysis", Morgan and Claypool Publishers, 2007.

Hampson, N.B. et al., "Reduction in Patient Timing Errors Using A Breathactivated Metered Dose Inhaler," CHEST, vol. 106, No. 2, pp. 462-465, Aug. 1994.

Dodds, L.J. Dodds et al., "Drugs in Use: Clinical Case Studies for Pharmacists", Pharmaceutical Press, 2010, Chapter 11: Asthma by Toby Capstick and Amy Vigar. pp. 212-234.

* cited by examiner

INHALER WITH TWO MICROPHONES FOR DETECTION OF INHALATION FLOW

CROSS-REFERENCE TO RELATED APPLICATIONS

This patent application claims the priority benefit under 35 U.S.C. § 371 of international patent application no. PCT/EP2015/055117, filed Mar. 12, 2015, which claims the benefit of European Patent Application No. EP14161419.8, filed on Mar. 25, 2014, These applications are hereby incorporated by reference herein.

FIELD OF THE INVENTION

The present invention relates to the field of medical devices, more specifically the invention provides an inhaler with two microphones for detection of inhalation flow.

BACKGROUND OF THE INVENTION

For the intake of medication for obstructive airways diseases, inhalers are well known. There are different types of inhalers, and each type has its own advantages and disadvantages. Nebulizer/compressor systems require minimal patient cooperation and coordination but are cumbersome and time-consuming to use. Metered Dose Inhalers (MDIs) are quick to use and highly portable, but require patient training to ensure coordination for proper use. Another type of inhalers are dry powder inhalers (DPIs).

An MDI typically has a housing, which is normally an all-plastic structure, into which a metal canister with a propellant can be inserted. The correct operation of the MDI is difficult since several actions must be performed subsequently: 1) Shake the inhaler before using, 2) Priming (firing in the air) when the inhaler was not used for several days, or in some other cases (a new canister, when the MDI has been dropped etc.), 3) Breathing out sufficiently to use the Function Residual Capacity (FRC) of the lungs as much as possible, 4) Firing (firing in the mouth), 5) Inhale for a sufficient duration (several seconds) to inhale the medication, and 6) Breath-hold for a sufficient duration to keep the medication in the lungs.

Thus, many mistakes can be made using an MDI. E.g. timing between the firing and the inhalation may be wrong, or the duration of the inhalation may be too short due to a too powerful inhalation, thus preventing the medication from reaching the deepest of the lungs. It has been found that 26-70% of patients using MDIs fail to inhale slowly and deeply, i.e. inhaling within the optimal flow rate of 25-60 liters per minute.

EP 1 993 642 B1 (Bang & Olufsen Medicom A/S) discloses an MDI with a microphone positioned in an add-on device for attachment to the MDI. The microphone captures sound in the frequency range 100-3,000 Hz which is used to determine e.g. an inhaling flow velocity. However, for normal environments with background noise, such a device may not be able to provide a reliable measure of flow velocity.

WO 2014/033229 A1 describes a system for monitoring user technique of an inhaler device with a microphone for sensing sound made during operation of the inhaler device. Inhalation and exhalation breath characteristics are analysed using temporal and spectral components. Frequency components may be analysed of the identified breath sounds, and means for classifying detected sounds as an inhalation or exhalation may be comprised. A second microphone may be used in line with the first microphone in order to differentiate between exhalations and inhalations.

SUMMARY OF THE INVENTION

Following the above, it would be advantageous to provide an inhaler that can teach or assist a user in obtaining a desired inhaling flow rate or flow velocity which can be used in a normal environment. Still further, it would be advantageous to be able to sense the flow rate during a user inhaling with low cost equipment. Yet further, it would be advantageous to provide an inhaler that can automatically identify different events during use of the inhaler, such as: priming, firing, and inhaling.

In a first aspect, the invention provides a system comprising an inhaler for dispensing aerosol or a dry powder, the inhaler comprising a housing comprising an air-inlet and a an air-outlet, wherein the housing defines a flow path between the air-inlet and the air-outlet, a first sensor arranged at a first position of an external surface of the housing, and a second sensor arranged at a second position of the external surface of the housing, wherein the first and second positions are spaced apart, wherein the first position is selected to have a shorter distance to the air-inlet than the second position, and wherein the first and second sensors are arranged to sense sound or vibrations resulting from a flow in the flow path, such as the flow being a flow of air (especially a mixture of ambient air with any one of: Aerosole and dry powder), and a processor arranged to process output signals from the first and second sensors according to an algorithm, so as to generate a measure of flow in the flow path, wherein said algorithm comprises an event classification part arranged to analyse the sound or vibrations sensed by the first and second sensors, so as to allow identification of at least one of event. Especially, the flow may be generated by a user inhaling from the air-outlet.

The inhaler is advantageous, since it has been verified that it is possible to sense a flow rate (flow velocity) within 15-120 liters per minute, specifically accurately within 25-60 liters per minute, based on the two spaced apart sound or vibration sensors, e.g. two microphones, to capture sound or vibrations on an external surface of the housing of the inhaler. Thus, when a user inhales a dose of aerosol or dry powder from the air-outlet of the inhaler, it is possible to determine a measure of flow, e.g. flow velocity or a temporal extension of the inhaling, based on the output from the first and second sensors. Thus, it is possible to determine if the inhaling flow is within predefined limits for correct use, thereby enabling feedback to the user regarding the inhaling procedure, e.g. whether inhaling is too strong, too weak, or correct. Further, the use of two spaced apart microphones further allows improved detection and classification of events during use of the inhaler, i.e. priming, firing, and inhalation, thus allowing determination of start and stop of such events, and thereby allowing evaluation whether the relative timing of these events is within prescribed limits.

The invention is based on the insight that with two such sensors, it is possible to effectively suppress background noise by using different signal processing techniques based on assuming that the two sensors capture essentially the same amount of background noise. Further, it has been found that it may be advantageous to limit the frequency range to the range 3-6 kHz in order to translate sensed sound or vibration signals, e.g. in the form of a measured sound pressure level, to a measure of flow in the flow path, e.g. flow velocity. It is to be understood that the specific mapping needed to translate from sound or vibration to the measure of flow may depend on the actual inhaler design. Thus, it may be required to provide corresponding measurements of sound/vibration and flow to obtain the precision needed for a specific inhaler device.

With an inhaler according to the first aspect, it is possible to quantify the inhaling flow with a high precision even in a normal environment with background noise, even though the captured signals resulting from the flow in the flow path inside the inhaler housing are rather weak. This allows a user to learn how to inhale at the most efficient flow rate, e.g. by a system providing the user with a feedback as to the inhalation force, after an inhaling procedure.

The positioning of the two sensors on an external surface of the inhaler housing allows application of the invention in the form of an inhaler training kit, where the two sensors are mounted on a structure that allows a user to attach and detach the sensors to a housing of existing inhaler types. The signal processing required to calculate a measure of inhaling flow may be provided in a separate processor unit that allows providing an output to the user in response to the calculated measure of flow to the user. E.g. such a separate processor unit may be in the form of a computer, a smartphone, or a dedicated device, arranged for wired or wireless connection with the first and second sensors and a processor unit. This may be applied in the form of adhesive tape or mechanical fixing means in the form of gripping arms etc. However, it is to be understood that in other embodiments, the inhaler may be a specific training inhaler with the two microphones mounted fixed to the inhaler housing.

The two sensors may further be used to detect other events in relation to the use of the inhaler, namely by applying classification algorithms to the sensed sound or vibrations, so as to determine timing of different events when using the inhaler. This may also be used to provide the user with feedback so as to teach the user a more appropriate use of the inhaler. It has been found that it is possible to provide an algorithm that automatically detects inhalation events only in response to the sound or vibrations picked up by the first and second sensors, and thus allowing a simple use of the inhaler. E.g. the inhaler may be fully automated, such as switching to an active state once it has been sensed that the inhaler is moved, e.g. sensed by using an accelerometer, e.g. being one of the first and second sensors.

The first position may be selected to be near the air-inlet, and wherein the second position is selected to be near the air-outlet. Hereby, the two sensors can be positioned at two positions of, or near, the flow path, and spaced apart. In one embodiment, the housing comprises a tube section, e.g. a straight tube section, with the air-inlet in a top end, and wherein a bottom end of the tube section is connected to a mouth-piece forming the air-outlet. Especially, a longitudinal axis of the mouth-piece is bent relative to a longitudinal axis of the tube section. In connection with such embodiment, the first position may be selected to be on a portion of the tube section at a distance of less than 30%, such as less than 20%, of a length of the tube section from its top end, and/or the second position may be selected to be on a portion of the tube section at a distance of less than 30%, such as less than 20%, of a length of the tube section from its bottom end.

The first and second position may be selected such that center positions of the first and second sensors are spaced apart by a distance of at least 1 cm, preferably at least 2 cm, e.g. a distance measured from center to center of the two sensors, or a distance based on the acoustical centers, in case the two sensors are microphones. The first and second positions are preferably selected to allow a substantial difference in the sound or vibrations sensed by the first and second sensors. Background noise may be more effectively suppressed, in case there is a considerable distance between the two sensors. However, in case the two sensors are microphones, it may be preferred that they are positioned on the same side of the housing, so as to effectively capture the same background noise, i.e. without being affected by different shadowing effects from the housing.

The first and second sensors may be mounted on a structure which is designed to allow a user to attach and detach the structure to said housing. E.g. a structure comprising one or more adhesive elements, or gripping arms, or clamps for attaching to the inhaler housing. Preferably, the structure serves to fix the two sensors in a fixed position relative to each other and the inhaler. In case of microphones, the structure may comprise an acoustic shield with one or more openings serving to ensure that essentially the same background noise reaches the two microphones. Alternatively, the structure comprises a shield serving to reduce background noise reaching the two sensors. The first and second sensors may alternatively be mounted on respective separate structures which are designed to allow a user to attach and detach the structure to said housing. Such separate structures allows e.g. a user to individually position the first and second sensors, e.g. allowing one kit to be used to different inhaler housings. The same ways of the just described attaching to the inhaler housing applies to such separate structures.

The first and second sensors may be selected from the group consisting of: microphones, strain gauges, piezo elements, accelerometers, bending sensors, capacitive sensors, magnetic sensors, displacement sensors, and optical sensors. Especially, the two sensors are of the same type, preferably identical sensors.

The housing is preferably arranged to receive a canister with a propellant in an opening, such as in an air-inlet opening.

It is to be understood that additional sensors may be used to supplement the first and second sensors. E.g. altogether three, four or even further spaced apart sensors, e.g. microphones, may be used to provide further information that can result in even further reduction of background noise, thus providing flow rate data with even further precision.

The algorithm may be arranged to generate the measure of the flow in response to a limited frequency range of the signals from the first and second sensors. Especially, such as the limited frequency range 2-7 kHz, such as 2-5 kHz, such as 3-7 kHz, 4-7 kHz, or 3-6 kHz, since it has been found that a level of sound or vibrations in such limited frequency range serves to provide a good correlation to a flow velocity in the flow path. Especially, it has been found that the frequency range 3 kHz to 6 kHz is sufficient to allow reliable determination of a measure of the flow rate at least in the range 25-60 liters per minute, but in general within a flow rate of 15-120 liters per minute. Thus, the algorithm may comprise bandpass filtering the signals from the first and second sensors to arrive at a band limited signal, e.g. with limit frequencies 3 kHz and 6 kHz, prior to determining the measure of flow.

Further, said algorithm comprises a noise suppression algorithm part for suppressing undesired background noise by utilizing a difference in the sound or vibrations sensed by the first and second sensors. Especially, such noise suppression algorithm part may comprise applying an adaptive beamforming part to the first and second sensor outputs, wherein the adaptive beamforming part is arranged to generate a first output indicative of a first noise suppressed signal. For further information, see e.g. EP 1 290 912

(Philips Electronics N.V.), or B. Widrow and M. E. Hoff Jr., "Adaptive switching circuits," in IRE WESCON Conv. Rec., 1960, vol. part 4, pp. 96-104, ISBN 0-13-605718-7. A further noise suppression step may be applied comprising a spectral subtraction in response to the output from said adaptive beamforming part, see e.g. S. F. Boll, "Suppression of Acoustic Noise in Speech using Spectral Subtraction," IEEE Trans. Acoustics, Speech and Signal Processing, vol. 27, pp. 113-120, April 1979.

Said algorithm may comprise calculating a level of sound or vibrations in response to an output from said noise suppression algorithm, i.e. based on a signal where influence from background noise is reduced, and translating said level of sound or vibrations to said measure of flow, e.g. a flow velocity. E.g. an average flow velocity during an inhaling period may be calculated in response to a sensed and background suppressed signal. E.g. a series of sound and vibration levels may be converted into a series of flow velocity levels, e.g. using a look-up table determined for the specific inhaler device, and in response thereto, an average flow velocity level may be calculated.

Further, said algorithm comprises identifying events related to an inhalation procedure in response to the output from the first and second sensors, and said algorithm may comprise signal detection and/or signal classification algorithm parts serving to identify an inhalation procedure, so as to allow automated use without any user inputs in the form of a push on a button etc. Further, said algorithm may comprises an event classification part arranged to analyse the sound or vibrations sensed by the first and second sensors, and identifying at least one of, or all of: a priming event, a firing event, and an inhalation event. Especially, said algorithm may comprise an event classification part arranged to analyse the sound or vibrations sensed by the first and second sensors, so as to allow identification of all of: a priming event, a firing event, and an inhalation event. This allows a fully automated product capable of identifying the critical events in using an MDI, and this is facilitated by the use of two spaced apart sensors, e.g. microphones.

The processor may be provided in a separate unit which is arranged to receive the first and second data in the form of a digital or analog signal provided by means of a wired or a wireless connection to the first and second sensors. Alternatively, the processor may be attached to or incorporated in an add-on structure arranged for attaching/detaching to the housing of the inhaler by a user without the use of tools. The first and second sensors may be provided in one single unit with gripping means or adhesive means arranged for being attached to and detached from the inhaler housing by the user, thus enabling the user to use e.g. different inhaler housings with only one set of sensors and processor. Especially, the processor unit may be a smartphone or a computer connected to the first and second sensors by means of a wireless connection (e.g.: Bluetooth) or a wired connection etc., wherein the processor in the smartphone or computer has been provided with a software application serving to execute said algorithm. In other embodiments, the processor is provided together with the sensors within one battery powered unit arranged for attaching to the inhaler housing.

The second position may be selected to have a shorter distance to the air outlet than the first position, thus allowing one sensor to be close to the inlet and one sensor close to the outlet, which helps identifying between priming and firing events.

Said algorithm may comprise an event classification part arranged to analyse the sound or vibrations sensed by the first and second sensors, so as to allow identification of at least one of: a priming event, and a firing event.

Said event classification part may be arranged to analyse differences in the sensed sound or vibrations from the first and second sensors, so as to distinguish between two events, e.g. a priming event and a firing event.

In one embodiment, the system comprises an inhaler for dispensing aerosol or a dry powder, the inhaler comprising a housing comprising an air-inlet and a an air-outlet, wherein the housing defines a flow path between the air-inlet and the air-outlet, a first sensor arranged at a first position of an external surface of the housing, and a second sensor arranged at a second position of the external surface of the housing, wherein the first and second positions are spaced apart, wherein the first position is selected to have a shorter distance to the air-inlet than the second position, and wherein the second position is selected to have a shorter distance to the air-outlet than the first position, and wherein the first and second sensors are arranged to sense sound or vibrations resulting from a flow in the flow path, such as the flow being a flow of air (especially a mixture of ambient air with any one of: Aerosole and dry powder), and a processor arranged to process output signals from the first and second sensors according to an algorithm, so as to generate a measure of flow in the flow path, wherein said algorithm comprises an event classification part arranged to analyse the sound or vibrations sensed by the first and second sensors, so as to allow identification of at least one of: a priming event, a firing event, and wherein said event classification part is arranged to analyse differences in the sensed sound or vibrations from the first and second sensors, so as to distinguish between the priming and the firing event.

In a second aspect, the invention provides a method for estimating a flow in an inhaler, wherein the inhaler comprises a housing defining a flow path between an air-inlet and an air-outlet, the method comprising receiving first data indicative of sound or vibrations sensed by a first sensor at a first position of an external surface of the housing, and wherein the first position is selected to have a shorter distance to the air-inlet than the second position, and receiving second data indicative of sound or vibrations sensed with a second sensor at a second position of the external surface of the housing, wherein the first and second position are spaced apart, and calculating a measure of a flow in the flow path by processing the first and second data according to an algorithm on a processor, identifying at least one event.

Said algorithm may be arranged to calculate the measure of the flow by processing a limited frequency range of the first and second data, such as the limited frequency range comprising the frequency range 2 kHz to 5 kHz, such as comprising the frequency range 3 kHz to 6 kHz. Especially, it has been found that the frequency range 3 kHz to 6 kHz is sufficient to allow reliable determination of a measure of the flow rate at least in the range 25-60 liters per minute, but in general within a flow rate of 15-120 liters per minute. Thus, the method may comprise filtering the first and second data to the limited frequency range, e.g. 3 kHz to 6 kHz, prior to applying further processing.

The algorithm may comprise a noise suppression algorithm part for suppressing undesired background noise captured by the first and second sensors. Especially, said noise suppression algorithm part may comprise applying an adaptive beamforming part to the first and second data, wherein the adaptive beamforming part is arranged to generate a first output indicative of a first noise suppressed signal and a second output indicative of a noise reference signal. The method may further comprise subtracting an adaptively filtered version of said second output indicative of a noise reference signal from the first output indicative of a first noise suppressed signal, and applying spectral subtraction to the resulting signal, so as to obtain a further suppression of the background noise.

The algorithm may comprise an event classification part arranged to analyse the sound or vibrations sensed by the first and second sensors, so as to allow identification of all of: a priming event, a firing event, and an inhalation event. E.g. this enables evaluation of relative timing between these event which is a crucial parameter in correct use of an inhaler.

In one embodiment, the method comprises receiving first data indicative of sound or vibrations sensed by a first sensor at a first position of an external surface of the housing, and wherein the first position is selected to have a shorter distance to the air-inlet than the second position, and wherein the second position is selected to have a shorter distance to the air-outlet than the first position, receiving second data indicative of sound or vibrations sensed with a second sensor at a second position of the external surface of the housing, wherein the first and second position are spaced apart, and calculating a measure of a flow in the flow path by processing the first and second data according to an algorithm on a processor, identifying at least one of: a priming event, a firing event, and analysing differences in the sensed sound or vibrations from the first and second sensors, so as to distinguish between the priming and the firing event.

In a third aspect, the invention provides a computer executable program code adapted to perform the method according to the second aspect when executed on a processor. Such computer executable program code is thus capable of performing the steps of the method according to the second aspect which can be implemented in software, e.g. as an add-on or modification of existing software in a ventilation device. The computer executable program code may especially be present on a non-transitory computer readable storage medium, or it may be loaded into memory of a processor system arranged to execute the program code.

It is appreciated that the same advantages and embodiments of the first aspect apply as well for the second, and third aspects. In general the first, second, and third aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
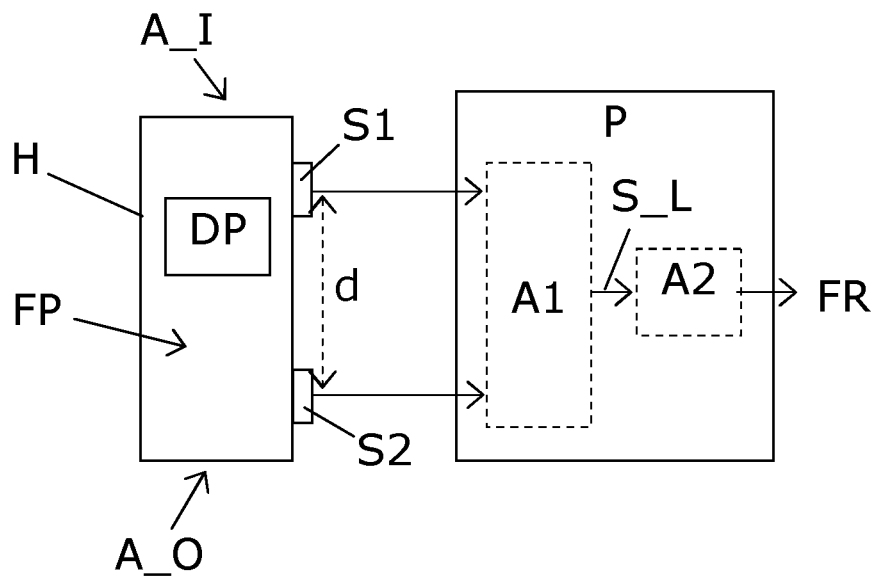
FIG. 1 illustrates a block diagram of an inhaler system embodiment.

FIG. 1 illustrates a block diagram of basic parts of an inhaler system embodiment comprising an MDI inhaler, two sensors S1, S2, and a unit comprising a processor P arranged for executing an algorithm with first A1 and second A2 algorithm parts, and resulting in outputting a flow rate FR, e.g. an average inhalation flow during inhalation. It is to be understood that the processor P may further execute an algorithm part (not shown) that classifies detected events into: priming, firing, and inhalation.

The inhaler has a housing H, e.g. a plastic housing, inside which a flow path FP is defined between an air-inlet A_I in a top part, and an air-outlet A_O in a bottom part. The housing H also contains a dispenser DP for dispensing a dose of an aerosol or a powder into the flow path, and preferably the opening forming the air-inlet A_I is arranged to receive a canister with a propellant. The user inhales the medicament through the air-outlet A_O, which may be formed as a mouth-piece.

Two sensors S1, S2, preferably small microphones, are positioned on the external surface of the housing H spaced apart by (center-to-center) distance d with the purpose of capturing sound resulting from air flowing in the flow path FP, thus allowing quantifying the flow in the flow path FP during an inhalation procedure. The first sensor S1 is positioned near the air-inlet A_I part, of the housing H, while the second sensor S2 is positioned near the air-outlet A_O part, of the housing H. It is preferable that the distance d is at least 1 cm, e.g. at least 2 cm, so as to ensure that the two microphones S1, S2 capture different sound signals from the noise in the flow path FP, i.e. by being placed outside and near two different parts of the flow path FP, but still such that they essentially capture the same background noise. To do so, it is preferable that the two microphones S1, S2 point in the same direction, or being positioned on the same side of the housing H, so as to ensure that they are being exposed to the same acoustical shadowing effect of the housing H. Depending on the sensors S1, S2, they may be attached, e.g. detachably, to the external surface of the housing H, either one by one, or mounted on one common structure to ensure that their relative distance d is fixed. However, the sensors S1, S2 may alternatively be permanently attached to the housing H, e.g. placed in or on dedicated structures monolithically shaped on the exterior part of the housing H.

The processor unit, e.g. a smartphone provided with a software application allowing execution of a first algorithm part A1 that is capable of receiving data indicative of the sound or vibration signals captured by the respective first and second sensors S1, S2, either in a wired or in a wireless form. The first algorithm part A1 applies a noise suppression algorithm for suppressing background noise picked up by the sensors S1, S2, utilizing the difference in the captured sound or vibration signals from the two sensors S1, S2. Details about some possible implementations of A1 are given later. The output from the first algorithm part A1 is a sound level S_L, or a series of sound levels measured during an inhalation procedure, wherein background noise has been suppressed. The first algorithm part may comprise an algorithm part arranged to detect start and end of events related to an inhalation procedure in response to the input from the two sensors S1, S2, so as to allow automatic determination of a set of data on which to apply the second algorithm part A2.

In the second algorithm part A2, this sound level data S_L is translated into a corresponding flow rate FR, e.g. using a predetermined look-up table of conversion factors between measured sound levels S_L and correspondingly measured flow rates FR for the specific inhaler design in question. Especially, it has been found that it is preferable to bandlimit the captured sound signals to the frequency band 3-6 kHz for providing an optimal mapping between measured sound and flow.

For monitoring correct-use of inhalers, there are two important uses: 1) Spot-check use by the clinician (expert's device) during visits of the patient to the clinician, and 2) Continuous use by the patient (trending device) to give feedback to user and/or the clinician.

Figure 2:
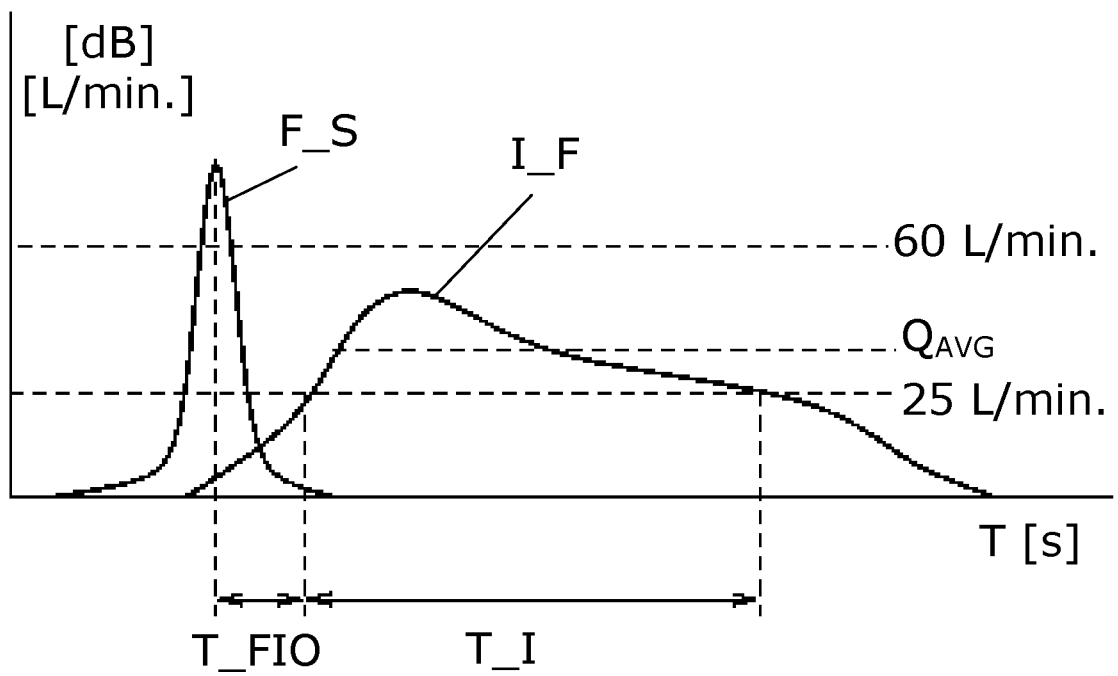
FIG. 2 illustrates clinical parameters for correct use of an MDI.

FIG. 2 illustrates an example of a graph showing a firing event followed by an inhalation as a function of time in the form of sound pressure [dB] measured for a firing event F_S and inhalation flow [L/min] measured for an inhalation I_F. Inhale-onset T_FIO or duration of inhale T_I are timing parameters that can be used to characterize the inhalation procedure. Cutoff rates for flow rate of a good inhale are typically set to 25 and 60 L/min. Another parameter that could provide information to a clinician could be the average flow $Q_{AVG}$ of the inhale procedure. Such parameters can be used to provide feedback to the clinician about correct-use and to objectively compare correct-use.

Figure 3:
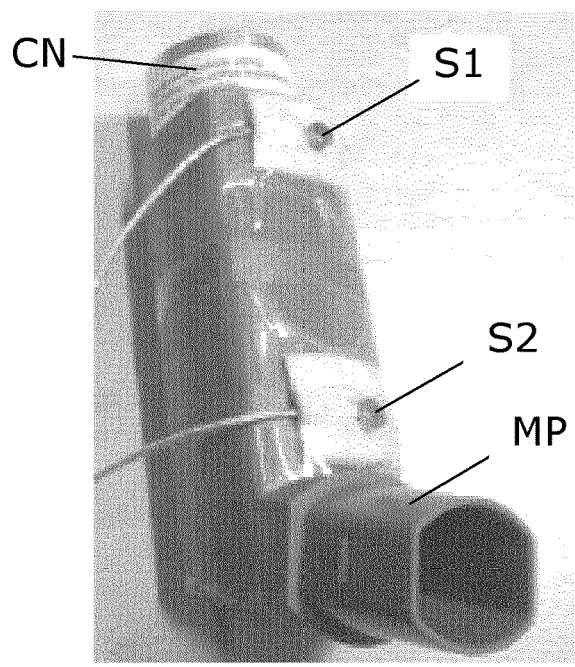
FIG. 3 illustrates a photo of an inhaler prototype with two microphones.

FIG. 3 shows a photo of a specific example of an inhaler with an air-inlet in the top part of the housing into which a canister CN with a propellant is received. The housing has a straight tube section with the air-inlet at a top end, and a bottom end of the straight tube section is connected to a mouth-piece MP forming the air-outlet, wherein a longitudinal axis of the mouth-piece is bent relative to a longitudinal axis of the tube section. Two small microphones S1, S2 are attached to the external surface of the housing in a test setup using tape. The first microphone S1 is positioned on a portion of the straight tube section at a distance of 10-20% of a length of the straight tube section from its top end, and the second microphone S2 is positioned on a portion of the straight tube section at a distance of 10-20% of a length of the straight tube section from its bottom end, namely close to where the mouth-piece MP is connected to the straight tube section. Wires for connecting the microphones S1, S2 are further seen.

The measured data shown and referred to in the following are measured with the test setup with the two microphones S1, S2 shown in FIG. 3.

Figure 4:
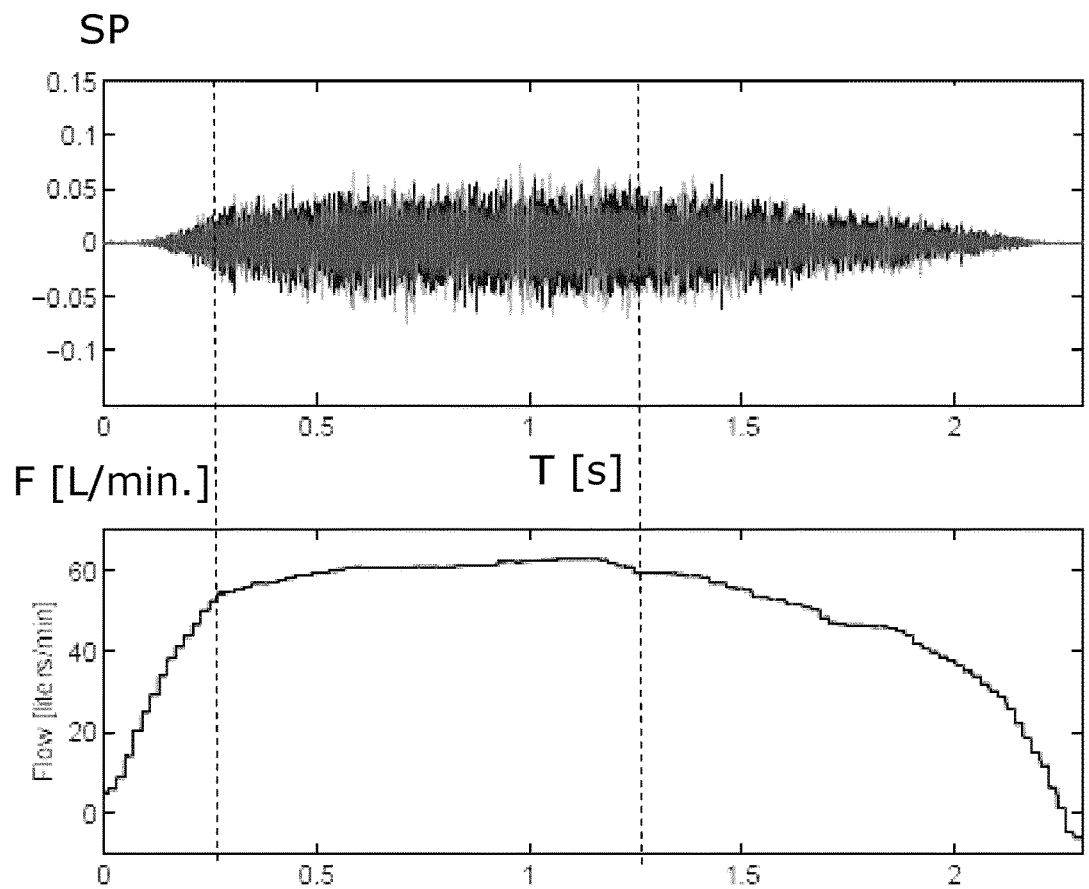
FIG. 4 illustrates an example of correspondingly measured sound and flow.

FIG. 4 shows the recorded sound response SP versus time of the two microphones S1, S2 sampled at 44.1 kHz (upper graph), together with a flow reference signal (lower graph) showing the corresponding flow velocity F [L/min.]. As seen, this corresponds to a scenario where an inhalation was performed with roughly 55-60 L/min over a period of one second (indicated by the vertical dashed lines). The sound from the top microphone S1 close to the air-inlet is louder compared to the sound from the bottom microphone S2 close to the mouth-piece (not visible since the two signals are overlaid). Further, it is seen that the amplitude of the sound approximately follows the flow velocity F.

During an inhale, the air is coming in through the top of the MDI causing turbulences which can be measured by sound. Because the microphone S1 at the top of the MDI is closer to the turbulences compared to the bottom microphone S2 and the mouth is wrapped around the mouth-piece, the bottom microphone S2 picks up significantly less sound compared to the top microphone S1. This level difference can be exploited to get rid of the environmental background noise.

Figure 5:
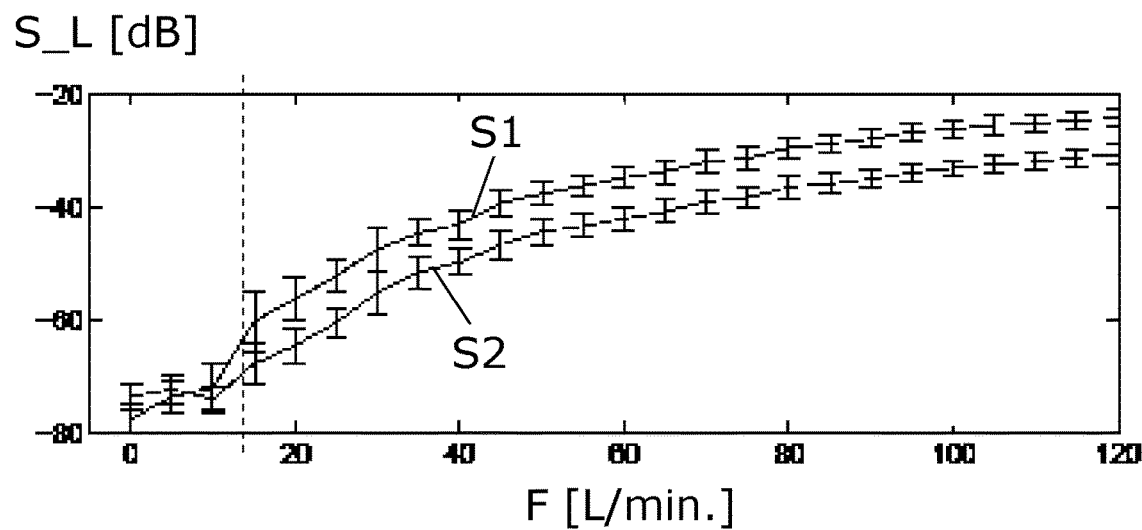
FIG. 5 illustrates an example of relation between measured flow and sound.

FIG. 5 shows measured sound level S_L [dB] picked up by the two microphones S1, S2 (filtered between 3 kHz and 6 kHz), plotted versus flow velocity F [L/min.]. As seen, there is a good flow-sound relation between 15 and 120 L/min, which is a sufficient range for analysing the flow during inhaling and for outputting the clinical parameters as described earlier. E.g. this allows establishing of a one-to-one conversion table or mapping between measured sound level (filtered between 3 kHz and 6 kHz) and flow. Below 15 L/min. (indicated by the dashed vertical line), it is not possible to reliably determine the flow based on the measured sound with the present test setup.

Figure 6:
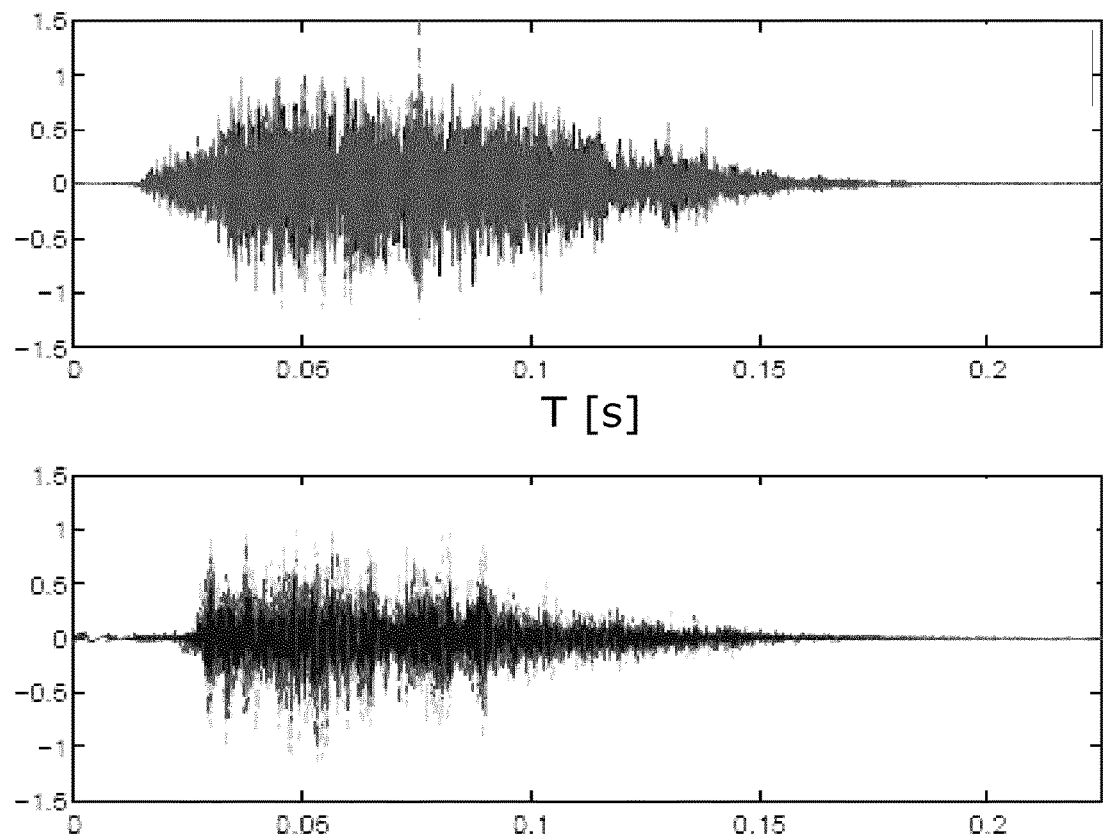
FIG. 6 illustrates examples of measure sound for firing and priming events.

FIG. 6 shows time waveforms for sound measured for a firing event (upper graph), and for a priming event (lower graph). The firing causes both microphones S1, S2 to have approximately an equal amount of energy in the sound (not visible), whereas for the priming there is a difference between the output from S1 and S2 (not visible). This difference can be explained by the fact that for firing the mouth is wrapped around the mouth-piece, and the signal on both S1 and S2 is effectively very similar. For priming, the mouth is not covering the mouth-piece and S2 thus captures a higher signal level. This difference between the firing and priming enables distinguishing between priming and firing to compute improved clinical parameters. For example, the clinician can see whether the priming occurred properly when the inhaler was not used for some longer time.

Figure 7:
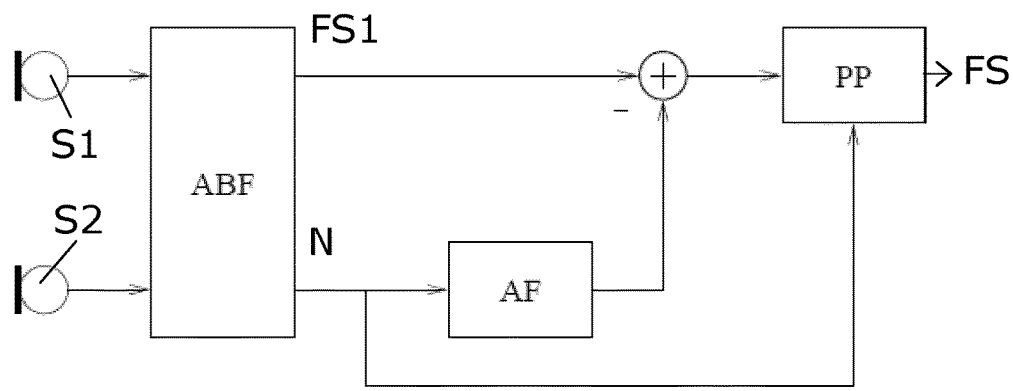
FIG. 7 illustrates a signal processing scheme for reduction of background noise from the two sensors.

FIG. 7 shows a block diagram of a scheme for suppressing background noise from the two microphones S1, S2, resulting in one noise suppressed output signal FS. The block diagram essentially corresponds to an example of the content of the first algorithm part A1 explained in relation to FIG. 1. The background noise may disturb the measurements, especially measuring low flows by an acoustic sensor. Separation of noise and flow components is possible however, when the two microphones S1, S2 are positioned close to the source (close to the air-inlet and air-outlet), and assuming that undesired noise sources are (much) further away from the microphones S1, S2. There are two main differences between an acoustic source in the nearfield (the sound generated by the flow) and an acoustic source in the farfield in a room environment.

The amplitude levels as measured by the microphones S1, S2 are about equal for the microphones S1, S2 for acoustic sources in the farfield, whereas the levels for a nearfield source can be different: the microphone closest to the source will measure a higher level than the one further away. The level differences for the MDI are up to 6 dB for frequencies from 100-3,000 Hz and flows from 10 L/min. to 100 L/Umin. In the frequency range 3-6 kHz, the 6 dB difference is found for flows above 40 L/min. (see FIG. 5).

For a source in the nearfield, there will be a delay if one of the microphones is closer to the source than the other. The average phase difference for a farfield source in a room outside the reverberation radius will be zero. For the lower frequencies (depending on the distance between the microphones) the noise components in the two microphone signals will be strongly correlated with equal magnitudes and zero phase difference.

Both differences can be used to separate a nearfield source from a farfield source. For events that are relatively strong with respect to the background noise like firing, priming and stronger inhalations, sufficient noise is already removed by subtracting the two microphone signals. Due to the strong correlation, especially the low frequency background noise is removed. For inhalations in particular, more noise suppression is needed, especially to be able to measure the flow accurately, at least in the range from 25 to 60 L/min.

A robust method is to use an adaptive beamformer block ABF (see e.g. the literature already referred to in the foregoing for further explanation). The ABF "beams" to the nearfield sound (i.e. the flow sound), and has a first output that contains a signal FS1 with an improved Signal-to-Noise-Ratio (SNR) regarding the background noise, but still contains a noise component. This is called the primary output of the ABF. A second output from the ABF is a signal N that contains almost no flow sound, but only noise. This is called a noise reference signal N. In case the noise reference signal N is correlated with the remaining noise in the primary signal, an adaptive filter AF can be used to estimate the remaining noise and subtracts it from the FS1 signal, thus resulting in an output which can be used in a post-processor PP, which uses also the noise-reference signal N of the ABF to suppress the noise even further. The post-processor PP works in the spectral domain and is known as spectral subtraction (see e.g. literature referred to in the foregoing). The ABF and AF have to be steered, i.e. the ABF has to adapt when the flow signal is dominant, whereas the AF has to adapt when the noise is dominant. To do this, a detector has been built using the amplitude difference on the microphones S1, S2: there is a significant difference if the flow signal is dominant, and almost no difference if the background noise is dominant. If the detector detects a significant flow signal the ABF is allowed to adapt and AF adaptation is stopped. In case only background noise is detected, the AF may adapt and ABF adaptation is stopped.

The adaptation of the ABF is the most critical one. In speech enhancement applications on top of the on/off detector described above, from information in the post-processor PP, it is possible to obtain an SNR estimate per frequency band and to use this information to adjust the adaptation speed per frequency based on the frequency dependent SNR. Because the acoustic source has a fixed position with respect to the microphone positions, at least no fast adaptation is necessary, and experiments have shown that for a given device, an initial training of the coefficients might be sufficient.

It has been shown that there is no need to take the full frequency bandwidth for deriving a sound level that can be converted into a measure of the flow, and the frequency band from 3 kHz onwards provides good correlation results, e.g. the band 3-6 kHz. Flows down to 15 L/min. (the lower bound for correct use), can be measured accurately when pre-processing is used up to a background noise level of 60 dB(A). With lower background levels also lower flow values can be measured, but this is only needed to indicate that the inhaling must be stronger.

In the following, the rationale behind detection and classification of sounds associated with MDI usage is given, such as for checking whether the MDI is used correctly. Firstly, it is desirable to automatically detect three different types of MDI sounds (events): priming, firing and inhalation.

Figure 8:
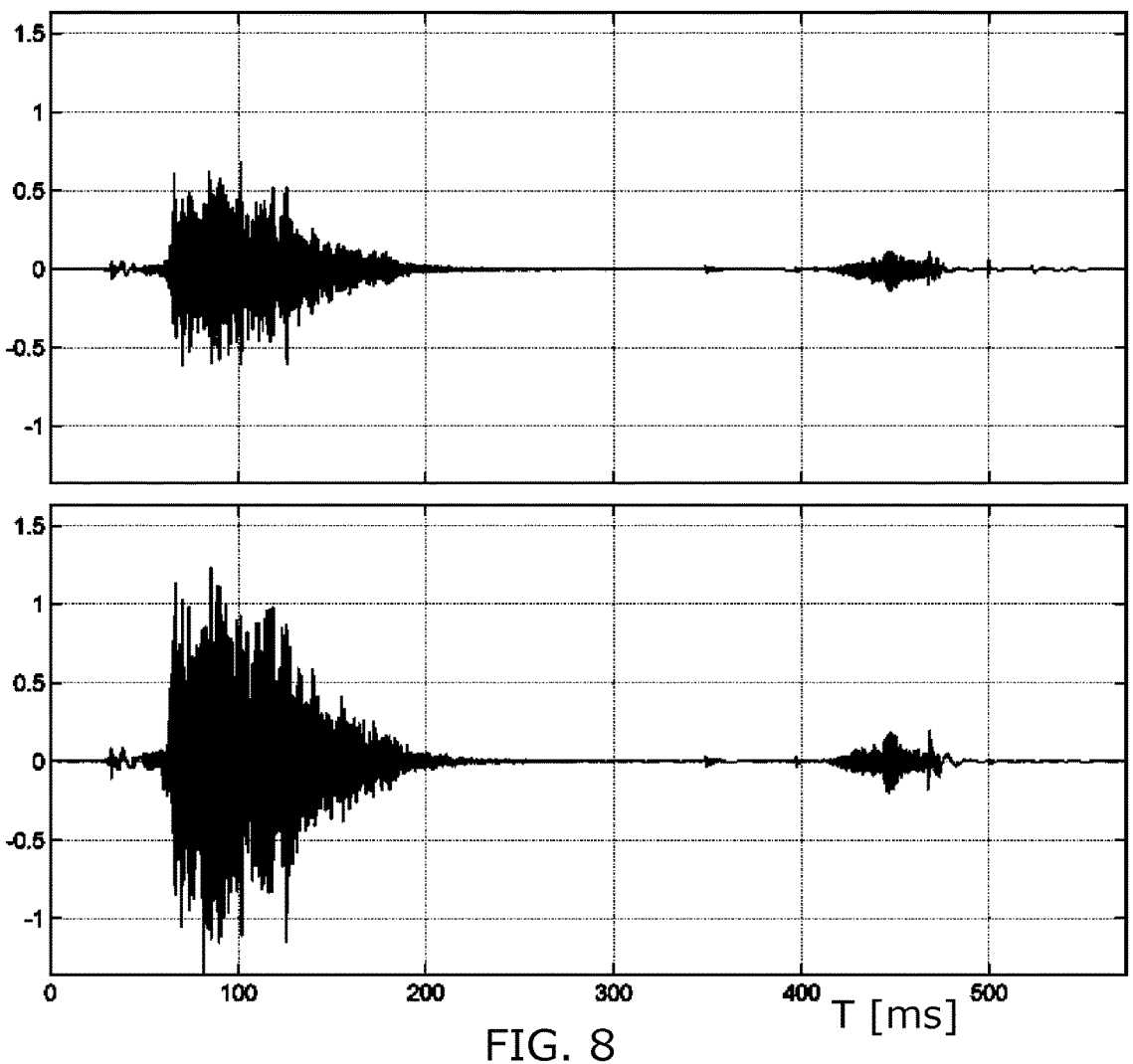
FIG. 8 illustrates an example of sound signals for a priming event.
Figure 9:
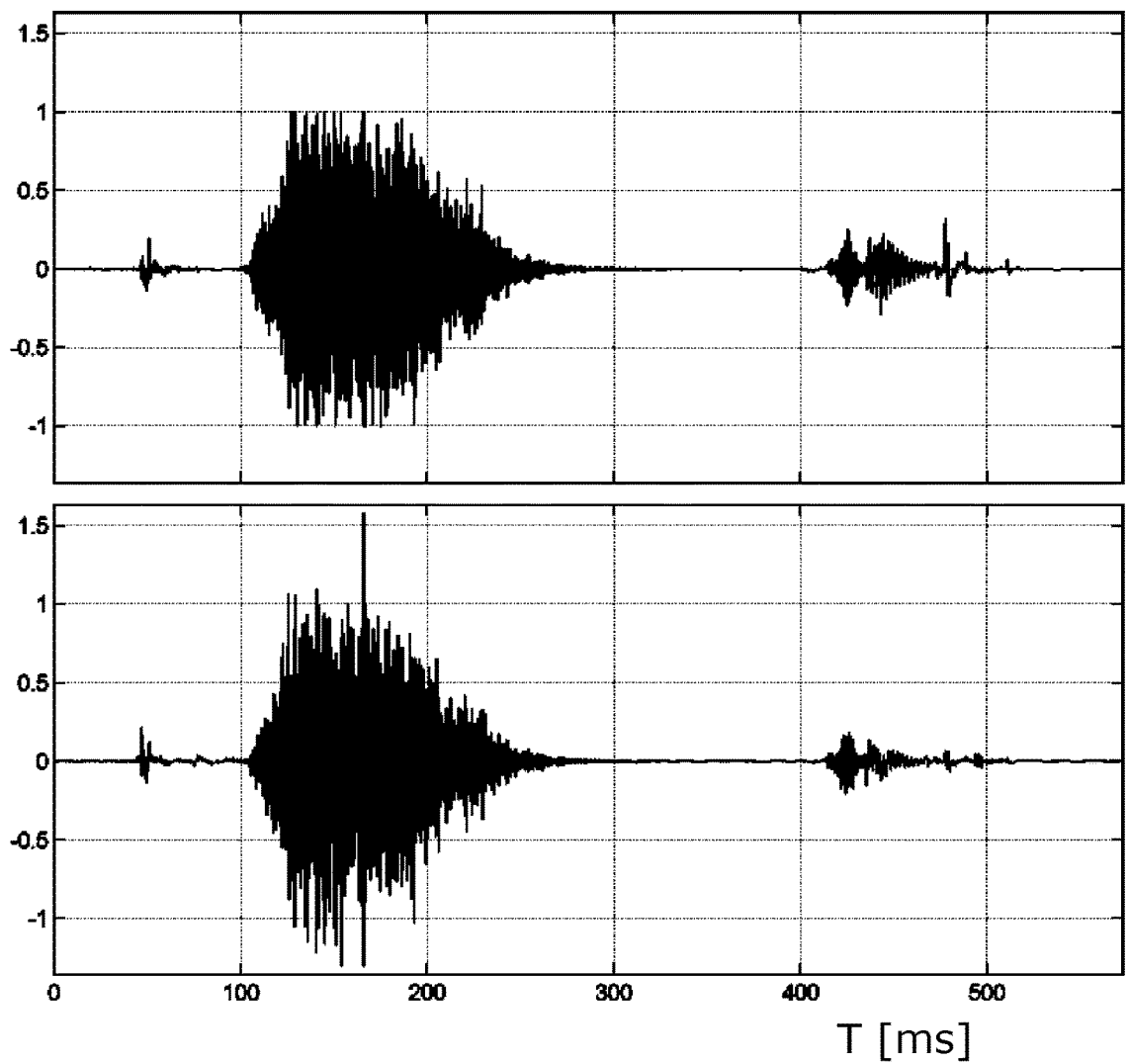
FIG. 9 illustrates an example of sound signals for a firing event.
Figure 10:
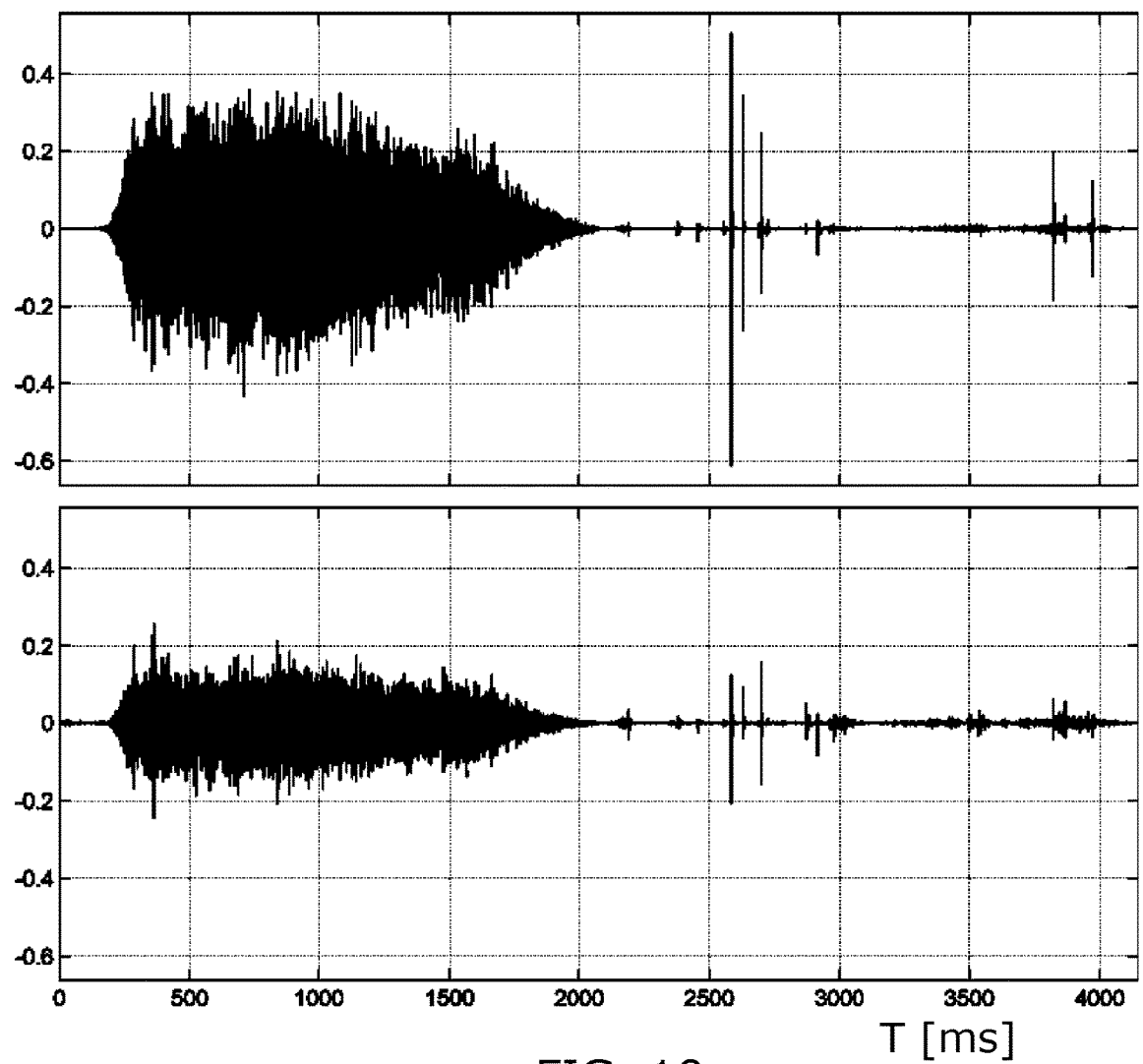
FIG. 10 illustrates an example of sound signals for an inhalation event.

FIGS. 8, 9 and 10 show examples of recorded sound versus time T with the two microphones S1, S2 for priming, firing, and inhalation, respectively. Sound from the top microphone S1 is shown as the upper graph, while sound from the bottom microphone S2 is shown in the lower graph. As seen in FIGS. 8 and 9, in the priming and firing signals, first there is a relatively large signal burst followed by a smaller burst. The first burst is generated by pressing the canister, and the second burst is generated by releasing it. FIG. 10 shows that in the inhalation signals first there is a relatively large signal burst, which is followed by several short signal bursts. The first burst is due to the inhalation, whereas the smaller bursts are due to rattles of the (mixing) ball in the canister that is caused by the movement of the inhaler when taking it away from the mouth.

Figure 11:
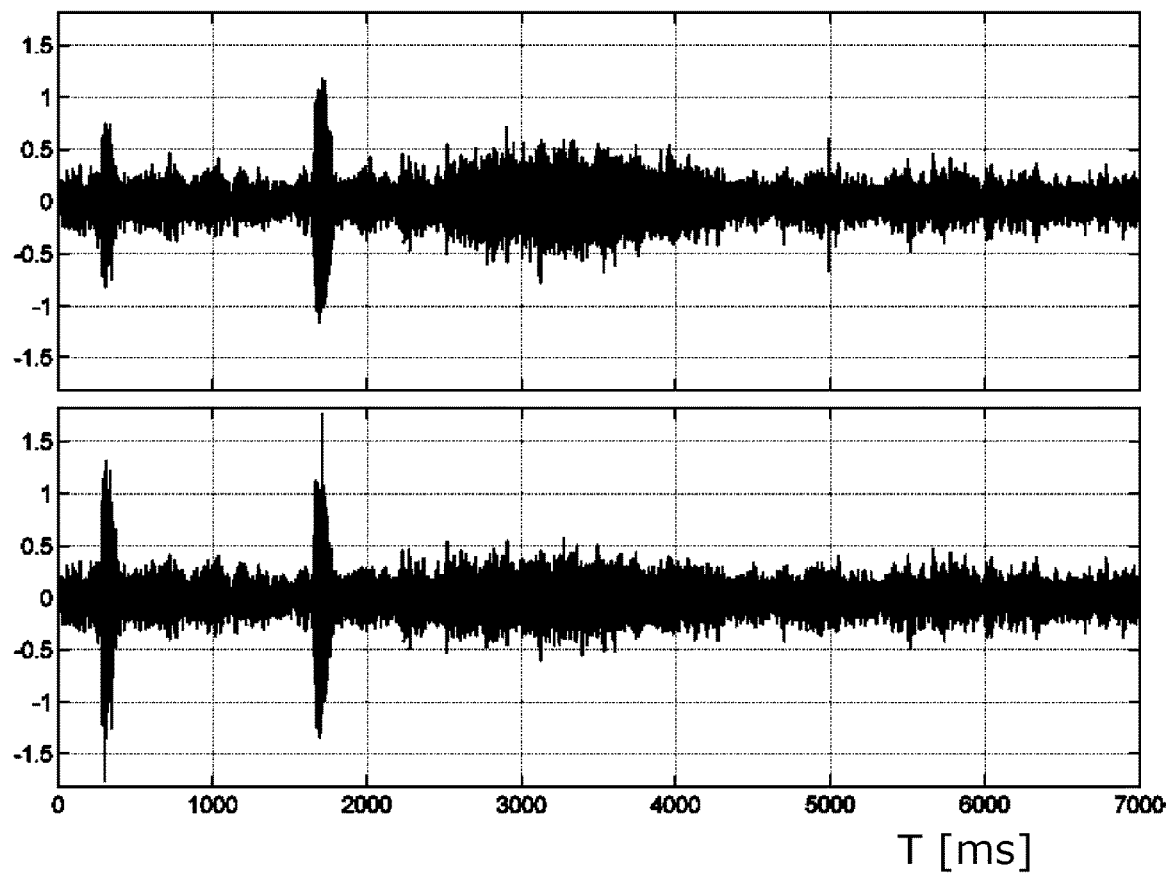
FIG. 11 illustrates an example of sound signals recorded for a sequence of priming, firing, and inhalation contaminated by strong babble noise.

FIG. 11 shows recorded sound versus time for a combined event with priming, firing, and inhalation contaminated by babble noise for the top microphone S1 (upper graph), and for the bottom microphone S2 (lower graph).

By 'detection' is understood determining whether MDI events are present in a given sound recording of the two microphones S1, S2 attached to the inhaler, as well as determining the start times, end times and durations of these events. Secondly, it is desirable to automatically classify the detected events into the classes: priming, firing, and inhalation. In combination with the start times, end times, and durations of the MDI events provided by the detection stage, the following additional information can be derived: 1) Order of MDI events, 2) Duration of inhalation, 3) Timing between firing and inhalation such as: a) time between (top or end of) firing and start of inhalation, b) early end of inhale after firing, c) firing after end of inhalation, 4) firing in second half of inspiration. This information can be used as input for diagnostic checks and/or conclusions. For example, it can be determined whether the different events were performed in the proper order, whether the inhalation was sufficiently long, etc. Clearly, the information can also be used for detecting long-term trends about the correct use of the MDI. The input(s) for the MDI event algorithm/method can either be the two microphone signals themselves, the output(s) of a noise reduction pre-processing stage, or a combination of these. The noise reduction can either be done on each channel individually, or it can use the two microphone signals to create a single enhanced signal.

Figure 12:
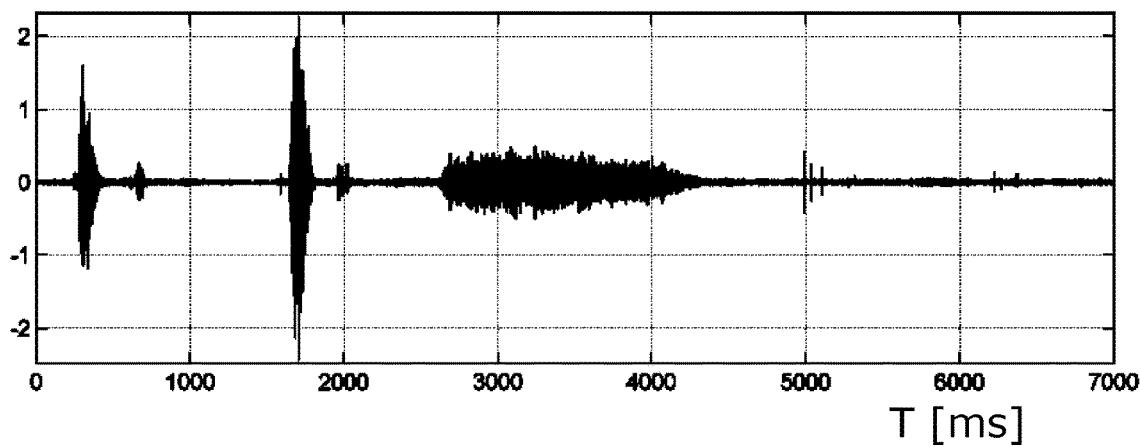
FIG. 12 illustrates a noise reduced version of sound signals from FIG. 11.

FIG. 12 shows an example of a single noise reduced signal computed in response to the sound input from the two microphones S1, S2 shown in FIG. 11. The algorithm is based on a sliding-window approach. Firstly, for each window of small duration, say 10-20 ms, the energy, Short Time Fourier Transform (STFT), and some features derived from the latter are computed. Then, the energy and feature curves as a function of the window index are post-processed by means of median filtering and smoothing. The resulting enhanced energy and feature curves are used as inputs to the actual detection and classification. It is assumed that components in the (raw or enhanced) microphone recordings that are due to the acoustic noise or interference are sufficiently small, such that the interesting MDI events rise above the noise level. This is clearly the case in the example of the noise-reduced recording shown in FIG. 12, and which will be used as an example in the following.

The detection of MDI events may be based on thresholding an enhanced version of the raw energy curve. Instead of energy, also mean absolute value or some other energy-like signal can be used. The times where the energy of the MDI events rises above the threshold determine the start times, end times and durations of the events.

Figure 13:
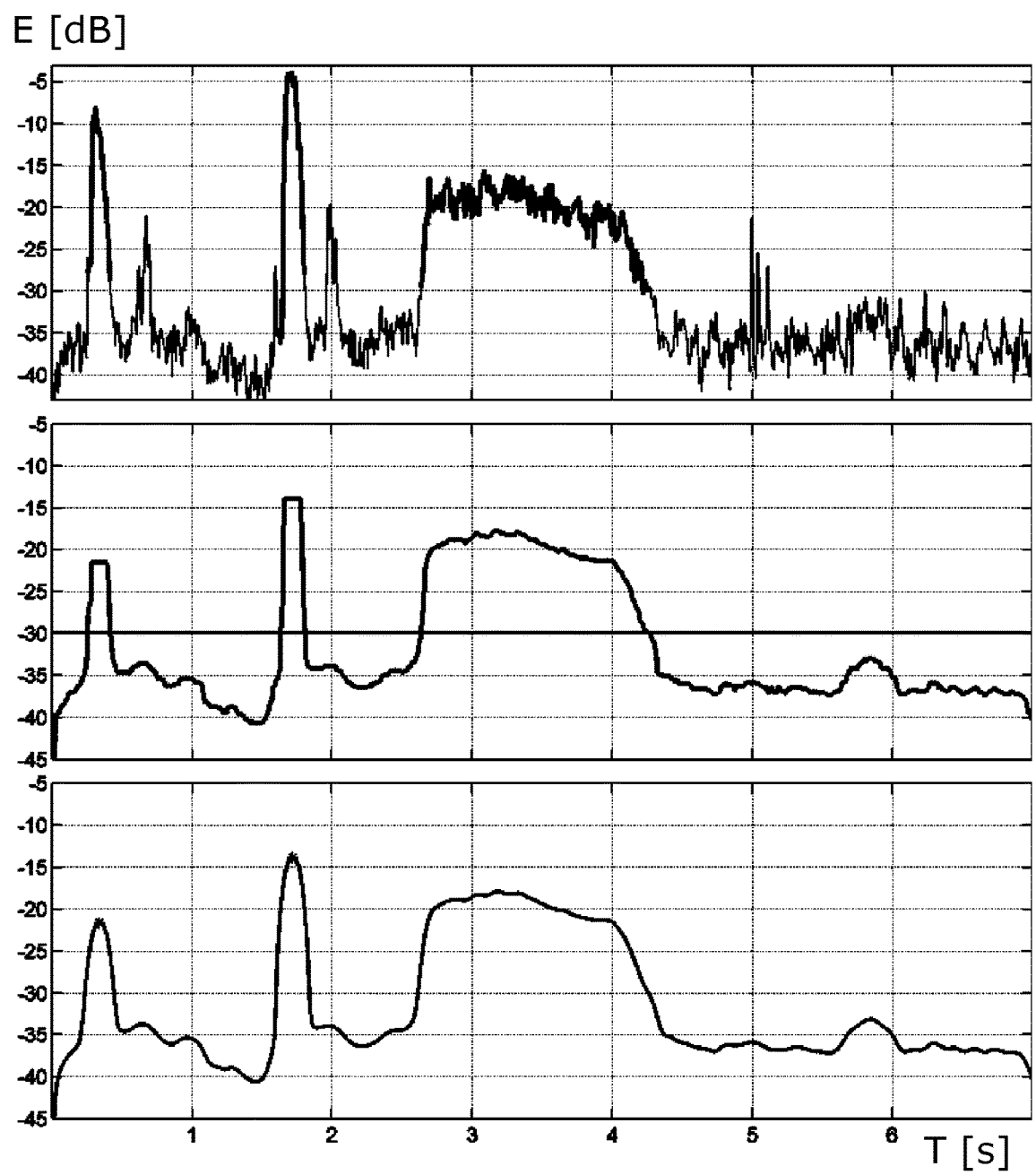
FIG. 13 illustrates thresholding and start/end time detection applied to the signal from FIG. 12.

FIG. 13 shows the results of applying the just described steps to the signal shown in FIG. 12, where all energies E are expressed in dB and plotted versus time T. The upper plot shows the energy computed from the signal in FIG. 12 as a function of the window index. The middle plot shows the result of filtering this window-based energy signal with a median filter. This signal is denoted by E(k), where k represents the window index. Finally, the output E(k) of the median filter is smoothed with a low-pass filter (LPF), the output of which is shown in the bottom plot of FIG. 13.

The detection of MDI events may be performed by thresholding the median filtered energy curve E(k) in the middle plot, or the curve in the lower plot that is a lowpass filtered version of the curve in the middle plot. The times where this signal rises above a certain threshold value determine the start times, end times and durations of MDI events. The threshold value is shown as a thick black line in the middle plot (at −30 dB) and is determined dynamically from the data as follows. Let E_dB(k) be E(k) as expressed in dB, i.e. $E\_dB(k)=10*\log 10(E(k))$. In addition, let E_prct (p) be the p-th percentile of E_dB(k) i.e. the value below which p percent of the values of E_dB(k) are found. Then the threshold for detecting MDI events in E_dB(k) is defined as follows:

$$E\_thr=\max((1-c)*E\_prct(p\_\min)+c*E\_prct(p\_\max), q)$$

where p_min is a low percentile, say between 0 and 5%, and p_max is a high percentile, say between 95 and 100%. The constant c can be chosen in the range 0.2-0.7. As an example c=0.4 has been used. The constant q imposes a minimum on E_thr. The threshold value E_thr is shown by the horizontal black line in the middle plot of FIG. 13. The parts that rise above the threshold defined the found MDI events. The left and right of each of these parts define the start and end time respectively of the associated MDI event. The signal in the bottom plot is used to find peaks in the segments that have been identified in the previous step and correspond to priming or firing. These peak locations can be used for timing computations.

In order to classify the detected events into: priming, firing, and inhalation, a two-step approach may be used. Firstly, distinguishing between priming and firing on the one hand, and inhalation on the other is done. This can be done based on the duration feature that is derived from the start and end times of the event(s). The duration of both priming and firing are much smaller than that of an inhalation. Priming and firing in general take less than 300 ms, whereas even very short inhalations take longer than 500 ms. Hence, this duration property is used to separate priming and firing on the one hand, and inhalation (and exhalations) on the other. Note that in practice the output of the block diagram of FIG. 7 may be used for detection of inhalation and the (possibly separately pre-processed) microphone signals for the detection of priming and firing. The second step is to distinguish between priming and firing. In order to achieve this, it is possible to exploit the fact that the power differences between the two microphone recordings are different for the two MDI events, but instead, or in addition, it is possible to exploit intrinsic properties of the respective event signals.

Figure 14:
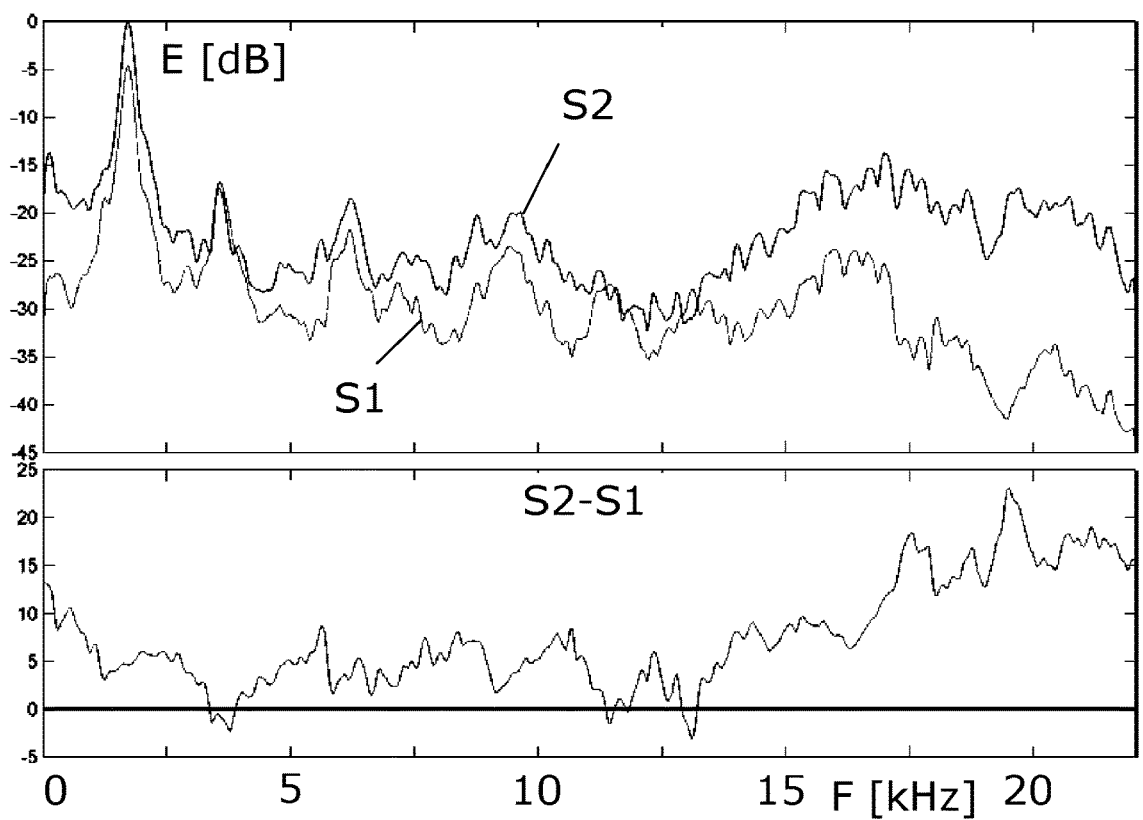
FIG. 14 illustrates examples of sound captured for a priming event: spectral power densities of two microphone signals and their difference.

FIG. 14 shows sound energy E [dB] for a priming event versus frequency F, for both microphones S1, S2. The energy of the bottom microphone S2 signal is significantly larger than that of the top microphone S1 signal over quite a wide frequency range. The lower graph in FIG. 14 shows the result for S2 subtracted by S1.

Figure 15:
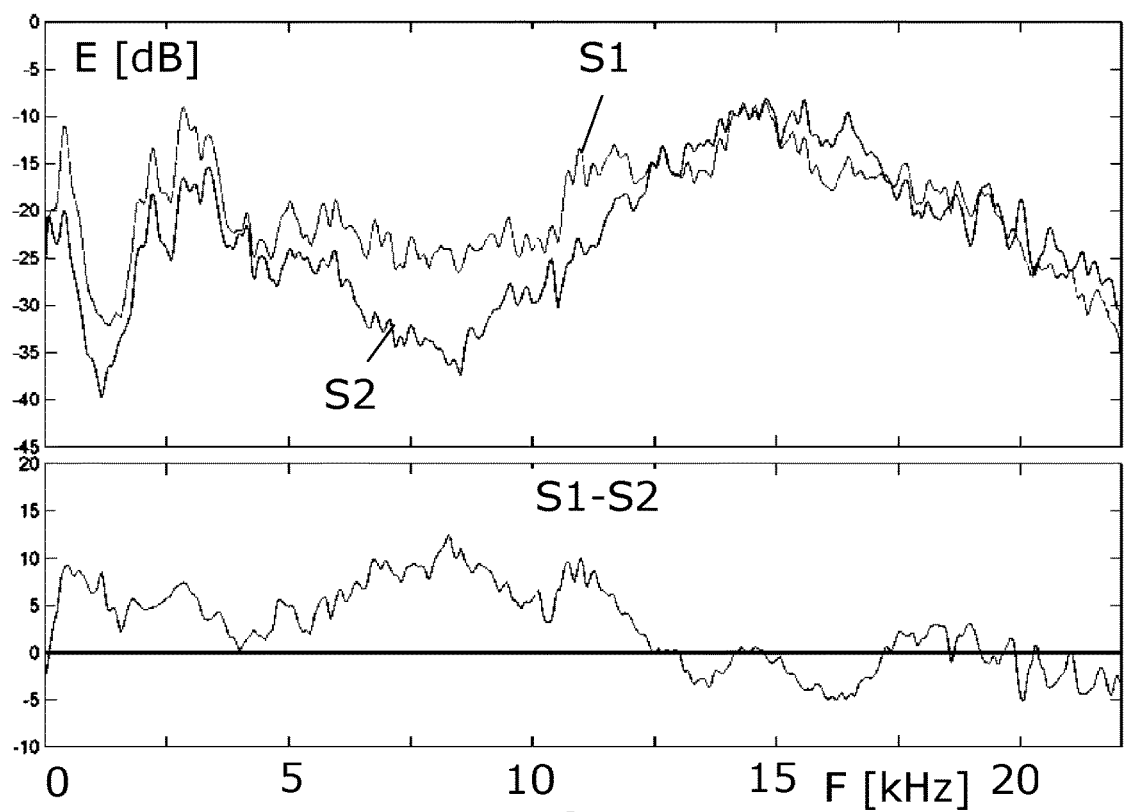
FIG. 15 illustrates examples of sound captured for a firing event: spectral power densities of two microphone signals and their difference.

FIG. 15 shows sound energy E [dB] for a firing event versus frequency F, for both microphones S1, S2. Here, the energy of the bottom microphone signal S2 is smaller than that of the top microphone S1 signal over quite a wide frequency range. The lower graph of FIG. 15 shows the result of S1 subtracted by S2.

The above features enable an easy distinction between firing and priming using ratios. E.g., for each detected event being either firing or priming, the ratio between the energy of the top and bottom sensor signals can be computed using only the part of the signals in the detected interval during which the event occurs (the two parts at the left of the middle and upper plots of FIG. 13). If this ratio is larger than a certain threshold, the event corresponds to firing, and when it is smaller, it corresponds to priming.

From inspection of spectrograms of a firing, main resonance frequencies vary over time. In particular, they become smaller as time progresses. On the contrary, from spectrograms of a priming, main resonance frequencies can be seen to be constant. This difference can be exploited in several ways: 1) For each event, it is possible to compute the difference between the (normalized) spectrum just after its start and the (normalized) spectrum just before its end, and normalize that (for example with the mean of these two spectra). Because the spectrum for firing changes significantly in time whereas that of priming changes much less, the (normalized) difference for firing is larger than for priming. 2) The spectral peaks for each window within a MDI event can be detected, e.g. with LPC, and check how much they vary with time. The variation for firing is larger than for priming.

Figure 16:
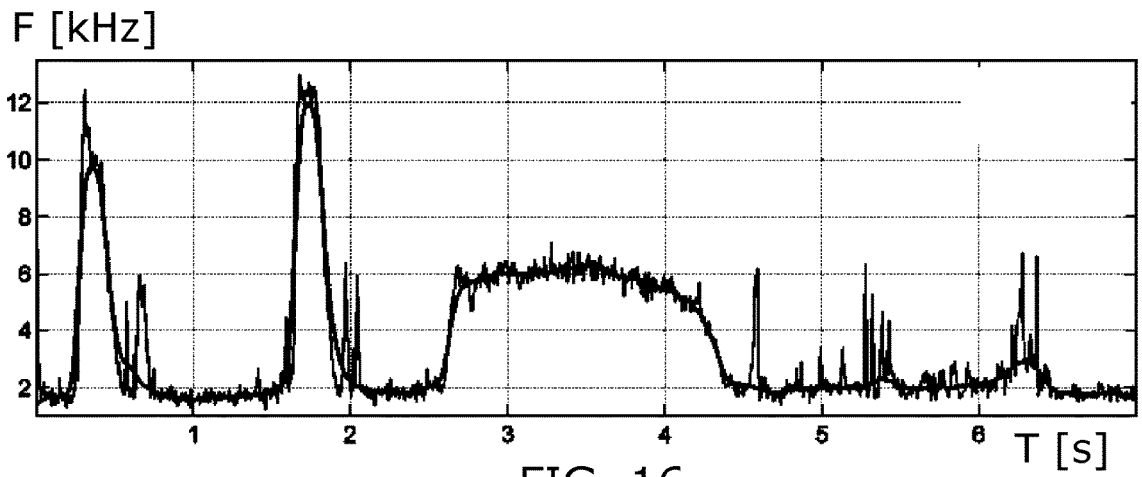
FIGS. 16 and 17 illustrate a spectral centroid, and a spectral bandwidth, respectively, calculated for the sound example from FIG. 12.
Figure 17:
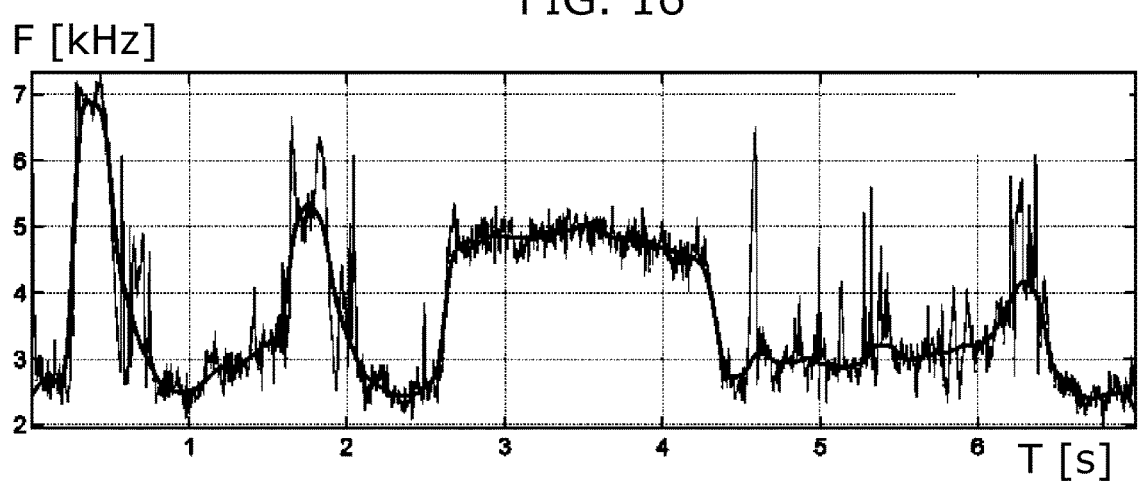

There are several other features that can be used for distinguishing between priming and firing, for example, the spectral centroid, spectral bandwidth or spectral median frequency. The spectral centroid and bandwidth of the signal in FIG. 12 are shown in FIGS. 16 and 17, respectively. The following properties can be observed: 1) The spectral centroid for firing is larger than for priming, 2) The spectral bandwidth for firing is smaller than for priming. In addition, both the spectral centroid as well as the spectral bandwidth can also be used (alone, or in combination with the energy) as input signals for the detection stage of the algorithm since they clearly show where the MDI events are located in time.

All features discussed above can be simultaneously exploited in a classifier such as a decision tree, a Support Vector Machine, etc.

Figure 18:
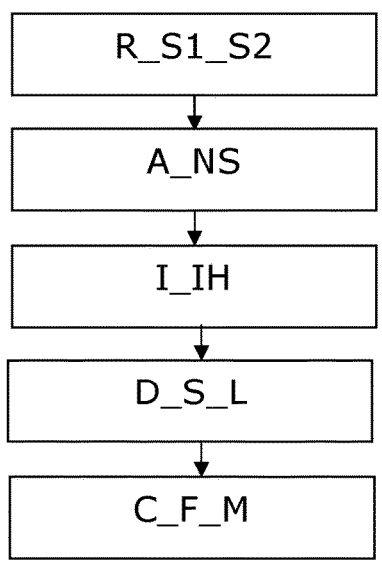
FIG. 18 illustrates steps of a method embodiment.

FIG. 18 shows an example of steps of a method embodiment. First, signals or data representing signals, from two sensors are received R_S1_S2. Then a noise suppression algorithm is applied A_NS, utilizing the difference between the sensed signals from the two spaced apart sensors, resulting in a single channel signal. The single channel signal is analysed with respect to identify start and end time of an inhalation event I_IH. Based thereon, the inhalation event is analysed with respect to determine a sound level, or a series of sound levels D_S_L during the inhalation event, and finally this series of sound levels are converted C_F_M to a measure of flow, e.g. a flow velocity or a series of flow velocities. A further step may be to compare the measure of flow with a reference or threshold value, so as to determine if the inhalation is within a predetermined boundary, or too strong or too weak.

To sum up, the invention provides an inhaler with a housing comprising an air-inlet and an air-outlet. Inside the housing a flow path is defined between air-inlet and air-outlet, where a dispenser is arranged to dispense an aerosol or a dry powder in the flow path. Two sensors, e.g. microphones, are positioned spaced apart at external surfaces of the housing to sense sound or vibrations resulting from a flow in the flow path at two different positions. This allows a precise detection of flow velocity during inhalation based on the sound or vibrations sensed by the two sensors, thus allowing examination of correct use of the inhaler. Further, the use of two spaced apart sensors facilitates identification of priming and firing events in the sensed sound or vibrations which may also be used in evaluating the use of the inhaler. Preferably, a noise reduction algorithm is used that exploits the differences in the captured sound or vibrations from the two sensors, so at to allow precise flow measurements even in noisy environments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An inhaler for dispensing aerosol or a dry powder comprising:
    a housing comprising an air-inlet and an air-outlet, wherein the housing defines a flow path between the air-inlet and the air-outlet, and
    a first sensor arranged at a first position of an external surface of the housing, and a second sensor arranged at a second position of the external surface of the housing, and wherein the first and second sensors are arranged to sense sound or vibrations resulting from a flow in the flow path, and
    a processor arranged to process output signals from the first and second sensors according to an algorithm, so as to generate a measure of flow in the flow path,
    wherein the first and second positions are spaced apart,
    wherein the first position is selected to have a shorter distance to the air-inlet than the second position,
    wherein the algorithm comprises an event classification part arranged to analyse the sound or vibrations sensed by the first and second sensors, to identify at least one event,
    wherein the at least one event comprises one or more of: a priming event, a firing event, and/or an inhalation event, and
    wherein the event classification part is arranged to distinguish between a priming and firing event on the one hand, and an inhalation event on the other based on a duration feature derived from start and end times of events, and wherein the event classification part is arranged to distinguish between a priming event on the one hand and a firing event on the other based on power differences between sound or vibrations sensed by the first and second sensors.

2. An inhaler according to claim 1, wherein the algorithm is arranged to generate the measure of the flow in response to a limited frequency range of the output signals from the first and second sensors.

3. An inhaler according to claim 1, wherein the algorithm comprises a noise suppression algorithm part for suppressing undesired background noise by utilizing a difference in the sound or vibrations sensed by the first and second sensors.

4. An inhaler according to claim 3, wherein the noise suppression algorithm part comprises applying an adaptive beamforming part, wherein the adaptive beamforming part is arranged to generate a first output indicative of a first noise suppressed signal.

5. An inhaler according to claim 3, wherein the algorithm comprises calculating a level of sound or vibrations in response to an output from said noise suppression algorithm, part and translating said level of sound or vibrations to said measure of flow.

6. An inhaler according to claim 1, wherein the housing comprises a tube section with the air-inlet in a top end, and wherein a bottom end of the tube section is connected to a mouth-piece forming the air-outlet.

7. An inhaler according to claim 6, wherein the first position is selected to be on a portion of the tube section at a distance of less than 30% of a length of the tube section from its top end.

8. An inhaler according to claim 6, wherein the second position is selected to be on a portion of the tube section at a distance of less than 30% of a length of the tube section from its bottom end.

9. An inhaler according to claim 1, wherein the first and second sensors are mounted on a structure which is designed to allow a user to attach and detach the structure to said housing.

10. An inhaler according to claim 1, wherein the first and second sensors are mounted on respective separate structures which are designed to allow a user to attach and detach the structures to said housing.

11. An inhaler according to claim 1, wherein the processor is arranged in a unit separate from the housing of the inhaler.

12. An inhaler according to claim 1, wherein the processor is incorporated in an add-on structure arranged for attaching and detaching to the housing of the inhaler by a user without the use of a tool.

13. An inhaler according to claim 1, wherein the second position is selected to have a shorter distance to the air outlet than the first position.

14. A method for estimating a flow in an inhaler, wherein the inhaler comprises a housing defining a flow path between an air-inlet and an air-outlet, the method comprising:
- receiving first data indicative of sound or vibrations sensed by a first sensor at a first position of an external surface of the housing;
- receiving second data indicative of sound or vibrations sensed with a second sensor at a second position of the external surface of the housing, wherein the first and second position are spaced apart, and wherein the first position is selected to have a shorter distance to the air-inlet than the second position;
- calculating a measure of a flow in the flow path by processing the first and second data according to an algorithm on a processor; and
- identifying at least one event by analysing the first and the second data, wherein the at least one event comprises one or more of: a priming event, a firing event, and/or an inhalation event, wherein distinguishing between a priming and firing event on the one hand, and an inhalation event on the other is based on a duration feature derived from start and end times of events, and wherein distinguishing between a priming event on the one hand and a firing event on the other is based on power differences between the first and the second data.

15. A non-transitory computer readable storage medium comprising executable program code arranged to perform the method according to claim 14, when executed by a processor.

* * * * *